United States Patent
Butler

(10) Patent No.: US 10,143,908 B2
(45) Date of Patent: Dec. 4, 2018

(54) SINGLE SQUAD MATCHUP PREDICTION POOL

(71) Applicant: Sylvester Butler, Okeechobee, FL (US)

(72) Inventor: Sylvester Butler, Okeechobee, FL (US)

( * ) Notice: Subject to any disclaimer, the term of this patent is extended or adjusted under 35 U.S.C. 154(b) by 0 days.

(21) Appl. No.: 15/886,779

(22) Filed: Feb. 1, 2018

(65) Prior Publication Data

US 2018/0154239 A1   Jun. 7, 2018

Related U.S. Application Data

(63) Continuation-in-part of application No. 14/296,388, filed on Jun. 4, 2014.

(51) Int. Cl.
  *A63F 9/24*    (2006.01)
  *A63F 13/00*   (2014.01)
  *G06F 17/00*   (2006.01)
  *G06F 19/00*   (2018.01)
  *A63B 71/06*   (2006.01)

(52) U.S. Cl.
  CPC .. *A63B 71/0616* (2013.01); *A63B 2243/0025* (2013.01)

(58) Field of Classification Search
  USPC ....... 273/440; 434/238; 463/2, 3, 20, 22, 25, 463/36, 43
  See application file for complete search history.

(56) References Cited

U.S. PATENT DOCUMENTS

| | | | | |
|---|---|---|---|---|
| 2005/0026123 | A1* | 2/2005 | Raniere | A63B 24/0062 434/247 |
| 2013/0045806 | A1* | 2/2013 | Bloodworth | A63F 9/24 463/43 |
| 2013/0288758 | A1* | 10/2013 | Jung | A63F 13/005 463/7 |
| 2014/0081437 | A1* | 3/2014 | Knapp | A63B 71/06 700/92 |

* cited by examiner

*Primary Examiner* — Adetokunbo O Torimiro
(74) *Attorney, Agent, or Firm* — Christopher J. Van Dam, PA; Chris Van Dam

(57) ABSTRACT

A process that utilizes single squad matchup predictions pools, non scoring forces possession changes, binary stats, players participants predictions, real-time or known statistical outcome that's compared to other squads, teams, individuals, positions, athletes, ranking and wagering based on a single contest or pool cumulative averages. Stat knowledge IQ differences allow players to control the outcome of their participation. It captures both offensive and defensive scores based on fans prediction IQ and not the actual game results, real-time, retro or fantasy. It is a self sustaining validating process.

5 Claims, 6 Drawing Sheets

| Enhanced Accuracy Ranking | Multiplier Effect on Base Stat Accuracy |
|---|---|
| 100% - 90% | +10% Increase to Base Accuracy |
| 90% - 80% | +8% Increase to Base Accuracy |
| 80% - 70% | +6% Increase to Base Accuracy |
| 70% - 55% | +4% Increase to Base Accuracy |
| 55% - 45% | No Change to Base Accuracy |
| 45% - 30% | -4% Decrease to Base Accuracy |
| 30% - 20% | -6% Decrease to Base Accuracy |
| 20% - 10% | -8% Decrease to Base Accuracy |
| 10% - 0% | -10% Decrease to Base Accuracy |

Fig. 4

Plus 1D
Enhanced Score Game Logic
**All Enhanced games will be weighted as follows

| Accuracy Rate In Enhanced Game Play Based On Pick'Em Selection | D-UP / O-UP Weighted Value Formula |
|---|---|
| 90% > | 10% Increase In D-Up / O-Up Value |
| 80% > | 08% Increase In D-Up / O-Up Value |
| 70% > | 06% Increase In D-Up / O-Up Value |
| 55% > | 04% Increase In D-Up / O-Up Value |
| no change 50% ±05 | No Change In D-Up / O-Up Value |
| 45% < | 04% Decrease In D-Up / O-Up Value |
| 30% < | 06% Decrease In D-Up / O-Up Value |
| 20% < | 08% Decrease In D-Up / O-Up Value |
| 10% < | 10% Decrease In D-Up / O-Up Value |

Fig. 5

| Number Off Ranking | Percent |
|---|---|
| 0 | 100% |
| 1 | 90% |
| 2 | 80% |
| 3 | 70% |
| 4 | 60% |
| 5 | 50% |
| 6 | 40% |
| 7 | 30% |
| 8 | 20% |
| 9 | 10% |
| 10+ | 0% |

Fig. 6

SINGLE SQUAD MATCHUP PREDICTION POOL

OTHER RELATED APPLICATIONS

The present application is a continuation-in-part of pending of U.S. patent application Ser. No. 14/296,388, filed on 4 Jun. 2014, which is hereby incorporated in its entirety by reference.

BACKGROUND OF THE INVENTION

1. Field of the Invention

The present invention relates to team sports, and more particularly, to a method for tracking performance and ranking the performance of teams compared to other teams.

2. Description of the Related Art

Several designs for comparing performance of sports teams have been designed in the past. None of them, however, includes a method to integrate the performance of defensive and offensive squads on a single team such that the performance value can be compared to the integration of defensive and offensive squads' performance on another team.

Applicant believes that the closest prior art is the traditional scoring methods of sports teams, such as American football, where the offensive squad is primarily responsible for acquiring points for their team. The present invention is different in, among other features, that it allows for the performance of the defensive squad on a team to contribute materially to the overall score of the team by achieving specified objectives beneficial to the team overall.

Several designs for sports scoring and game-player predictions skill and measures of practical sports knowledge have been designed in the past. None of them, however, includes a multi-factor system utilizing plural aspects of defensive and offensive sports performance to determine a game-player's actual predictive skill level and knowledge of particular teams, squads and players.

Other patents and methods in the public domain describe other means to rank and score teams that provide for a number of more or less complicated elements that fail to solve the problem in an efficient and economical way. None of these patents suggest the novel features of the present invention.

SUMMARY OF THE INVENTION

It is one of the main objects of the present invention to provide a team sports scoring method that allows the skill and performance of a defensive squad materially contribute to the overall score of the team as a whole.

It is another object of this invention to provide a way to increase the volatility of scoring by altering the dynamics of team sports strategy to enhance the spectator experience.

An object of the present invention is to reduce the effects of luck or randomness of a score and increase the value to the overall score that skill of formerly non-scoring players bring to the game.

Another object of the invention is to more accurately demonstrate the value of individual players on a squad that may have a significant impact on recruiting, drafting and player placement, among other factors.

It is still another object of the present invention to provide a method to reduce occurrences that can result in inequitable outcomes of the game from situations such as sudden death or overtime.

It is one of the main objects of the present invention to provide a system and method applied to single squad team fantasy matchup pools to quantify a gameplayer's prediction skills of future outcomes.

It is another object of this invention to provide a computer system and method to determine a comparative measurable and empirical value of a gameplayer's statistical knowledge of at least defensive athletic performance during a game.

It is still another object of the present invention to provide a gameplayer's skill valuation to compare to other fantasy team sports gameplayer's to rank and order relative predictive skill and knowledge levels.

It is yet another object of this invention to provide such a method and device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 4 shows a table of multiplier effects.
FIG. 5 shows a table of weighted value formula.
FIG. 6 shows a table of ranking adjustment factors.

DETAILED DESCRIPTION OF THE PREFERRED EMBODIMENT

Figure 1:
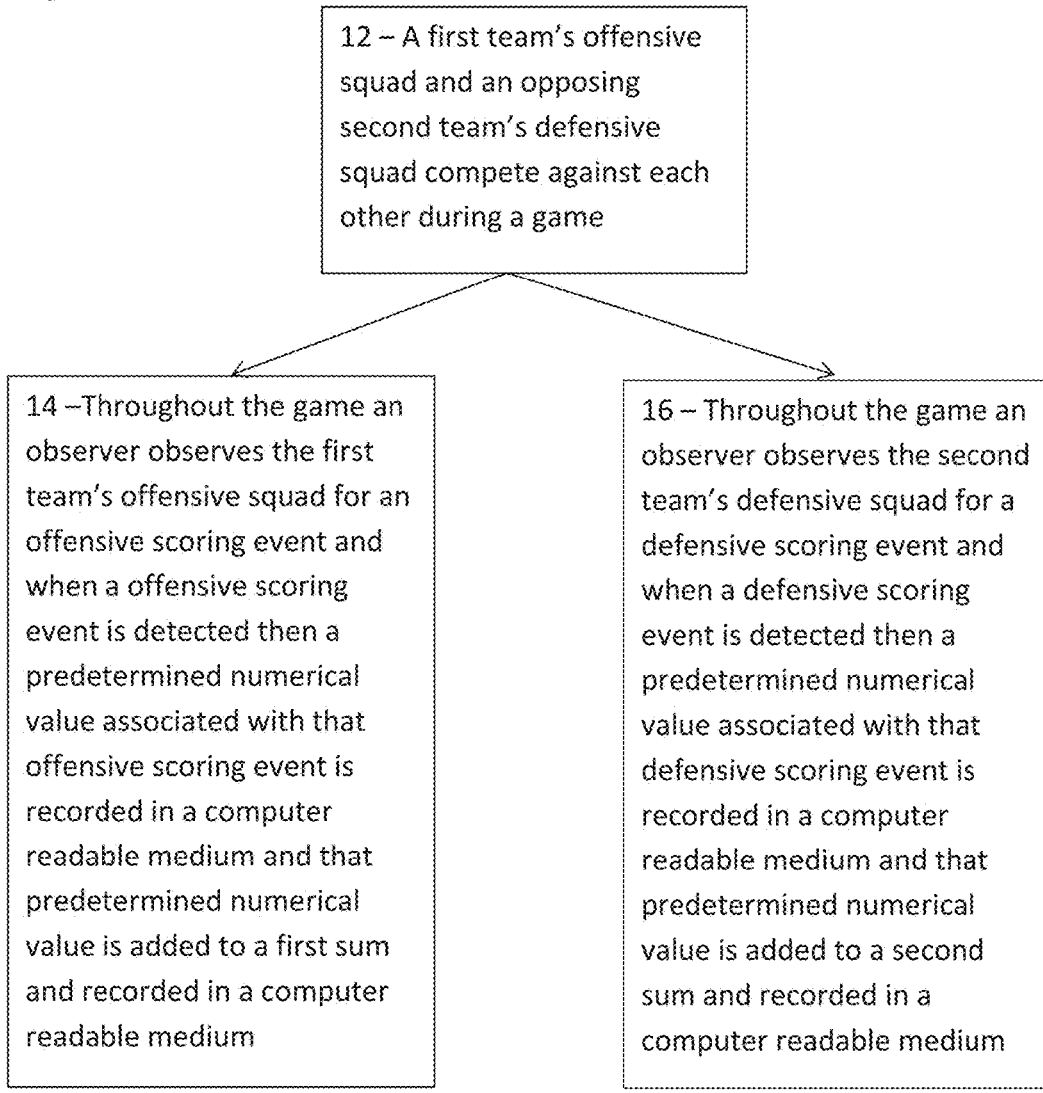
FIG. 1 represents a flow chart of a process.

While this invention may be embodied in many different forms, there are described in detail herein specific embodiments of the invention. This description is an exemplary of the principles of the invention and is not intended to limit the invention to the particular embodiments illustrated and described.

For the purpose of this disclosure, like reference numerals in the figures shall refer to like features unless otherwise indicated or is obvious by context.

The subject system and method of use is sometimes referred to as the device, the invention, prediction pools, the pick'em game, the statistical knowledge game, the system, the software, the machine or other similar terms. These terms may be used interchangeably as context requires and from use the intent becomes apparent. The masculine can sometimes refer to the feminine and neuter and vice versa. The plural may include the singular and singular the plural as appropriate from a fair and reasonable interpretation in the situation.

Team sports have been an American, and indeed worldwide, tradition for many years. Billions of dollars are spent by fans watching, listening to and obsessing about sports.

Along with great tradition, there are some imperfections with common conventions for comparing one team to another team. It is not always the best team that wins any particular game, match, series, bout, contest or other type of competition.

Sometimes, due to factors beyond the control of the individuals on a team or the team as a whole, the result of the completion is decided on factors other than simple superiority on one team over another on a simple score.

For example, in many sports there are squads or designated players that primarily act as defenders while other members perform more as offensive players. In many cases the lines between defensive players and offensive players are blurred because the same player can at one instant be defending and at another instant close in time, even in the same sortie, can take on an offensive role.

For example in basketball or soccer a player and team can be advancing the ball offensively in one moment and then they can quickly loose possession and become defenders, trying to prevent the opposing team from scoring against them.

In many sports there is little opportunity for a defensive player or defensive squad to directly contribute to the score of the team. Points are awarded in far greater numbers to the offensive squad of that particular team.

This is not to mute the benefit that a well-qualified defensive squad can contribute to the team. To the contrary, the importance of a robust defense cannot easily be overstated. The value in limiting the scoring opportunity to an opposing team is frequently the critical advantage that many teams have that push them towards success and prove superiority over a competitor.

Some of the examples described herein refer to American football. It is intended that the disclosure herein is also readily applicable to other sporting scenarios. Applications can be made with team sports or other team endeavors.

The methods can also be applied where there are not distinct offensive squads and defensive squads, per se. Any defensive action can be assigned a point or numerical value to contribute to an overall score where traditionally points have only been awarded for more formal offensive actions.

A method or a system for more accurately determining the skill level of a team with more precision than simply adding up offensive scoring is needed to better address the complexities of the contributions of defensive players and defensive squads in a team sports setting is needed to better decide a winning team.

Non-scoring forced possession changes, as contrasted to forced scoring possession change, are combined and result in every possession change that either the defense squad achieves or that the offensive squad achieves will be combined to determine the defensive score.

A single squad on a single team consisting of a defensive characterized squad and an offensive characterized squad are compared to any other single squad on a single team alone or combined with other teams or squads.

The system is used to observe a single squad on a single team by itself or combined with other teams or squads in real time or for statistics from a team or squad that competed in a contest.

The system then identifies any actual possession changes and categorizes them to identify all non scoring forced possession changes as being credited to a defensive or special teams category or to identify any forced scoring possession changes as offensive or special teams category. The system then assigns a point value for each possession change based on a predetermined value of the type of forced possession change.

A user of the system selects the style or type of tournament. In one example, stats or pick'em style games are set up. The user makes a squad selection from a real life or fantasy contest, either exclusively or combined. The game points can be calculated by the system in real time or can be based on recorded stats from a prior game. The results of the user's performance is based on that user's stat knowledge and predictive ability to know the outcome of the contests better than other users.

The system can optionally have available a metric that allows users the opportunity to increase or decrease the overall stat knowledge intelligence quotient (IQ) based on the accuracy of users predictions.

The system can capture actual statistical results for any single squad from real life or a fantasy contest, singly or combined, with real time or previously recorded stats from a former contest. The system then computes and compares that specific user's average prediction per squad to actual statistical results per squad for stat. The closer the predictions of that player are to the actual outcome of the contest the higher that user's IQ. This can be based on percentages or ranking in real life or a fantasy contest, singly or combined based on real time results or previously determined stats from a prior contest.

When the predetermined contest is completed the system determines a winner based on stat IQ per squad average or enhanced ranking or per squad cumulative score. This then may be combined or enhanced by the average stat knowledge IQ ranking of that user and others.

Looking now in more detail at the system logic, the following is exemplary and illustrative, but not limiting, as to how the system process and the users interact with the system.

There are generally three types of user roles that will be considered in the system platform:

Admin User—This user is basically a representative of the system operator who will be able to perform the following functions in addition to the overall management of the system:

Create Contests—these contests will be considered featured platform contests;

Cancel contests;

View contests reports;

This user may not participate in any contest;

This user may not receive winnings from any contest.

Standard Users—These users are the regular users of the system and who will be able to perform the following functions:

Interact with other users on the platform (aka system);

Invite friends to join the platform;

Create contests;

Join and compete in contests;

View their own standing in contests;

Receive winnings from contests.

Celebrity Users—These users consist of verified celebrities and other influencers who will promote the system/platform in exchange for a share of the profits generated in the contest. These users must be verified by the admin user who will be responsible for creating their account. These users will be able to perform the following functions:

Create contests—these contests will be considered featured celebrity contests;

View contest reports for their own created contests;

Join and complete in contests;

View their own standing in contests;

Receive winnings from contests;

Looking more specifically at the contests it can be appreciated that contests are the basic element of gameplay and user interaction. Contests generally involve two or more users who willingly participate in a competition consisting of making predictions about some aspect of one or more sporting events. These contests may have a financial cost to the user and may also have a financial reward for the predetermined set of winning positions at the end of the contest.

Primary contest types can be broadly characterized as:

Stats based contests—Stats based Contests are a basic foundation of the platform. These games require a participating user to assign a set of prediction values related to a team's performance during a particular game. The user will predict in-game statistics and be graded on the accuracy of these predictions.

Pick'em contests—Pick'em contests are an additional set of contests in which users can participate. These contests require a user to predict the performance of several teams in a given set of matchups. Users will need to pick one team from each of the matchups in the entire set and make their overall prediction for this team. Like stats contests, pick'em will also require the user to make specific predictions about in-game events. Pick'em contests will have all the options that are available for Stats contests including Enhanced Stats.

Stats based contests offer various types of gameplay options for participating users. There are various branches of stats based contests. For example:

Defense based contests—These contests will place a strong emphasis on the prediction of stats related to defensive actions that occur during a game or contest of any variety;

Offense based contests—These contests will emphasize the prediction of stats related to offensive actions that occur during a game;

Combined contests—These contests will be a combination of both defense and offense predictions that occur during one or more games depending on the user's selected team(s);

Stats Contest Levels

In addition to these main branches of stats based contests there are two levels of gameplay for each of these branches.

Base stats: These contests involve making predictions on specific statistics that correspond to either an in-game scoring event or a non-scoring forced change of possession during the game including:

Defense base stat contests will be referred to as D-UP Contests;

Offense base stat contests will be referred to as O-UP Contests;

Combined base stat contests will be referred to as combined stat contests;

Users will predict the number of these events that may occur throughout a game and will be ranked on how accurately they predict the number of these events.

Base Enhanced Stats:

These contests are the second level of gameplay and will build on the base stat predictions;

Enhanced Stats will serve to complement the base stats score by adjusting the base score as defined in the enhanced score logic schedule;

Users will predict a several in-game statistics that relate to either defensive or offensive actions that occur in the game depending on the selected base stats;

Enhanced Stats may include aggregate and average statistics for a single game;

Enhanced Stats will be weighted in order to provide an even level of comparison for all the different stats included in the predictions;

Stat Enhancements will be applied to the base stat according to the branch.

Contest Duration

When creating a contest the user who sets it up will decide on the duration of the contest. A contest will contain as many games as are allotted during the contest duration period. The available choices for contest duration are:

One Day Contest—The user will select the Date for the contest and only the teams who will be playing a game on the set date would be available to choose for this contest.

Weekly Contest—The user will select the week for the contest. A weekly contest may require users to pick for multiple games depending on the sport. In this case the week will be loosely defined so that all teams have the same number of games available in the contest. For example, the weekly contest may last up to ten calendar days or could be from mid-week to mid-week. All teams in the league may be available for weekly contests.

Season Contest—Season contests may begin at any point before or during the season. Season contests will begin according to the next game number for all teams. Since all teams play the same number of games, but these games are not played on the same day necessarily, the season will begin on the next available game number for all teams in the league. Season contests will last from the start date to the end of the season. Not all season contests will contain the same number of games. This will depend on their creation date. All players in a particular contest will pick for the same number of games.

Contest Participation

All contest participants will be enrolled for the entire duration of the contest. Once a contest begins, no other users may join the contest and no users may drop out of the contest. Any user who wishes to drop out and not make selections will simply receive a minimum rating for the contest.

Stat Contest Results

Users will be ranked according to the score they receive based on the accuracy of their predictions for all games encompassed in the contest period. The user with the highest accuracy score is determined to be the winner of the contest. This score will also be maintained throughout the platform in a user metric that maintains the user's average score. This will be described in detail in the user score section, below.

Ranking all elements allows for ranking of each single squad based on the non scoring force possession changes statistical binary process for, but not limited to, the best scoring defensive squad.

The platform will maintain the following scores to determine the contest winner(s):

Defense Based Contests

D-UP (defense up) score—this is the score obtained from the base stat predictions in a defense based contest; This will be the final score for a D-UP Contest; This score will be added to the user's average D-UP score; This score will determine the winner for the D-UP contest;

Enhanced Score—this is the score obtained from the enhanced stat predictions in a contest.

Enhanced D-UP Score—this is the score obtained when taking the base D-UP score and applying any modifications offered by the enhanced score results. This will be the final score for a D-UP enhanced contest. This score will be added to the user's average D-UP score. This score will determine the winner for the D-UP Enhanced contest.

Offense Based Contests

O-UP (offense up) score—this is the score obtained from the base stat predictions in an offense based contest. This will be the final score for an O-UP contest. This score will be added to the user's average O-UP score. This score will determine the winner for the O-UP contest.

Enhanced score—this is the score obtained from the enhanced stat predictions in a contest.

Enhanced O-UP score—this is the score obtained when taking the base O-UP score and applying any modifications offered by the Enhanced Score results. This will be the final score for an O-UP enhanced contest. This score will be added to the user's average O-UP score. This score will determine the winner for the O-UP enhanced contest.

Combined Stat Contests

Base scores—these are the scores obtained from the Base portion of the stat contest.

D-UP Score—this is the score obtained from the Defensive Base Stat predictions in the contest. This will represent half of the final score for a combined contest. This score will be added to the user's average D-UP score. This score will be averaged with the O-UP score to determine the contest winner.

O-UP Score—this is the score obtained from the offensive base stat predictions in the contest. This will represent half of the final score for a combined contest. This score will be added to the user's average O-UP score. This score will be averaged with the D-UP score to determine the contest winner.

Enhanced Scores—these are the scores obtained from the enhanced stat predictions.

Enhanced D-UP score—this is the score obtained when taking the base D-UP score and applying any modifications offered by the enhanced defense score results. This will represent half of the final score for an enhanced combined contest. This score will be added to the user's average D-UP score. This score will be averaged with the enhanced O-UP score to determine the contest winner.

Enhanced O-UP score—this is the score obtained when taking the base O-UP score and applying any modifications offered by the enhanced offense score results. This will represent half of the final score for an enhanced combined contest. This score will be added to the user's average O-UP score. This score will be averaged with the enhanced D-UP score to determine the contest winner.

Total score—this is the score obtained when averaging the final D-UP and O-UP scores for a contest. Base contests will average the base D-UP and base O-UP scores to obtain a final score. Enhanced contests will average the enhanced D-UP and enhanced O-UP scores to obtain a final score. This score will determine the contest winner.

Contest Form

There are three contest forms which may be defined for stat contests. All stat contests will fall into one of these form categories. These contest forms, however, are dependent on the contest style. They will determine what options will be available to the user when selecting their team(s) or squad.

Default Form—This form is available for base and enhanced contests when playing offense only or defense only branches of stat contests. Users will select a single team for which to make either defense or offense predictions depending on the selected branch.

Straight Form—This form is available for both combined base contests and combined enhanced contests. Users will select a single team to make their base offense and base defense predictions. In the case of combined enhanced contests, users will make both offense and defense enhanced predictions for the same team for which they predict base stats.

Fantasy Form—This form is available only to combined enhanced style contests. Users will select one team for their defensive stat predictions and a different team for offensive stat predictions. Users will make enhanced defense predictions for the same team for which they predict base D-UP (defensive up) stats. Users will make enhanced offense predictions for the same team for which they predict Base O-UP (offensive up) stats. In a Fantasy Contest users will not be allowed to pick the same team for both offense and defense.

Squads

A Squad is defined as the selection of team(s) that will be used in order to make predictions throughout a stats based contest. Every contest will require that the user pick a squad in order to participate.

Picking a Squad—In order to participate in any stats contest, users must pick a squad. Depending on the contest options, a squad may consist of a single team or of a combination of two different teams where one is picked for defense predictions and the other for offense predictions.

Defense Based

D-UP contests pick one team for making base defense predictions. D-UP enhanced contests pick one team for making both base defense predictions and enhanced defense predictions.

Offense Based

O-UP contests pick one team for making base offense predictions. O-UP enhanced contests pick one team for making both base offense predictions and enhanced offense predictions.

Combined

Straight base contests pick one team for making base defense and base offense predictions. Straight base contests pick one team for making base defense, base offense, enhanced defense and enhanced offense predictions. Fantasy Base Contests pick one team for making base defense predictions and pick a different team for making base offense predictions. Fantasy enhanced contests pick one team for making base defense and enhanced defense predictions and pick a different team for making base offense and enhanced offense predictions.

Making Predictions

Once a user has selected a squad he will be required to setup predictions for the next upcoming game that is featured in the contest according to the contest duration period.

Defense Based

D-UP contest—Users will make predictions for all D-UP stats according to the D-UP stats list for the contest sport.

D-UP basic enhanced contest—Users will make predictions for all D-UP stats and all enhanced defense stats according to the enhanced stats list.

Offense Based

O-UP contests—Users will make predictions for all O-UP stats according to the O-UP stats list for the contest sport.

O-UP Basic Enhanced Contest—Users will make predictions for all O-UP stats and all enhanced offense stats according to the enhanced stats list.

Combined

Combined base contests—Users will make predictions for all D-UP stats according to the D-UP stats list and users will also make predictions for all O-UP stats according to the O-UP stats list.

Combined enhanced contests—Users will make predictions for all D-UP and O-UP stats as well as predictions for all enhanced defense and enhanced offense stats according to the enhanced stats list.

Other Contest Options

When setting up a contest there will be a limited number of options available to the user. Some of these options will only be available for specific contest types and forms.

Team fan contest—This option will limit all users who participate in the contest to pick for only one specific team which will be specified by the user who creates the contest during the contest creation process. For fantasy contests the contest host will pick the fantasy team by combining one offensive squad with one defensive squad. All participants will need to enter predictions for this same fantasy team combination for the duration of the contest.

There is an optional stat contest tie breaker—In order to mitigate the possibility of users tying at the end of a stat contest, there will be a tie breaker for all stats contests regardless of contest form or branch. Along with each set of predictions, users will need to enter pick'em style predictions for the current game(s) being picked for the stat contest predictions.

Single game predictions—All D-UP, O-UP, defense enhanced, offense enhanced, straight base and straight enhanced contests will require users to predict the game outcome for the game their selected team is playing.

Double game predictions—All fantasy contests will require that users predict the game outcome for each of the games that their two selected teams are playing in.

Single Fantasy Predictions—In the event that a user two selected teams are actually playing each other in a fantasy contest, the user will only make one game prediction predicting the stats contest tie breaker users will select one of the two teams in the matchup(s) and predict the following values for the selected team:

D-UP (defense up) score—this is the total number of D-UP points scored by the selected team in the game according to the system.

Game score—this is the total number of regular points scored by the selected in the game.

"+1D" Score—this field will be calculated based on the sum of the D-UP Score and the game score.

Game winner—pick which team will win the game, a user can predict the score for a team that will not necessarily be the game winner Scoring the Stats Tie Breaker The tie breaker will be scored according to the accuracy of the predictions entered for the matchup(s) including, for example, accuracy predicting final D-UP score, accuracy predicting final O-UP (offense up) score and accuracy predicting Game Winner according to "+1D" score.

Any of the described contests that involve individual predictions is a stats contest and can be played in pick'em style. Multiple games with individual prediction are stats played pick'em style.

Pick'em Contests

Pick'em contests are similar to stats contests but will involve predicting defense and offense stats for multiple teams. Users can set up pick'em contests to include any number of games that will occur in the upcoming contest round. These contests will require users to make predictions for all match-ups that are included in each round of the contest. For example, users will predict for one of the two teams in each matchup; users can pick any of the two teams in a matchup to predict; predictions can be based on the "+1D" scoring method; users will be ranked according to the accuracy of their predictions.

Pick'em Contest Types

Pick'em contests will have two main types of contest setup. The gameplay can effectively remain the same for these two contest types. The user who sets up the contest will determine the contest type and based on this will make a series of selections to which all users who participate in the contest will need to adhere for their entries.

Straight Pick'ems

Straight Pick'ems are based on current real-world matchups where the teams available to select will be playing each other on the field. The user who hosts a straight pick'em contest will select which matchups will be included in the contest. The available matchups will be determined by the contest length and the contest round. Each participating user will be able to make their predictions according to each matchup based on the contest branch selected by the host user.

Fantasy Pick'ems

Fantasy pick'ems are not necessarily based on real-world matchups and can consist of any combination of squads for both offense and defense which can be matched up with any other combination of squads. The squads available to select when building a fantasy pick'em contest must be playing in an active game during the contest duration period and the current contest round time frame for multi-round contests. The user can host a fantasy pick'em contest will first need to select the number of games which will be included in the contest. Once the number of games is determined the user must select an offense squad and a defense squad for each team in each matchup included in the contest. There can be a possible combination of up to four team squads involved in any particular matchup. A single squad may only be used in one matchup for each contest round. Each participating user will be allowed to select their team to make predictions based on the contest branch.

Pick'em Contest Branches

There may be three branches for pick'em contests. Players will be able to choose from different contests branches when creating a contest. All contest entries will be making predictions based on the contest branch.

Defense Only Branch—This branch will involve making defense based predictions only throughout the contest.

Offense Only Branch—This branch will involve making offense based predictions only throughout the contest.

Combined Branch—This branch will involve making both defense and offense based predictions throughout the contest.

Pick'em Contest Levels

There will be several levels of gameplay for pick'em contests very similar to stats contests where users will be able to make predictions for different sets of stats.

Base Stats—This level will involve making predictions for only D-UP (defense up) and/or O-UP (offense up) based stats. Participating users will pick one team from each matchup in the round to predict stats. Defense only pick'em contests may be referred to as D-UP pick'ems. Offense only pick'em contests may be referred to as O-UP pick'ems. Combined pick'em contests will be referred to as simply pick'ems.

Enhanced Stats

This level will augment the Base Stat predictions with Enhanced stats. Participating users will pick one team from each matchup in the round to predict base D-UP and/or O-UP stats as well as enhanced defense and/or enhanced offense stats. Enhanced defense pick'em contests will be referred to as enhanced D-UP pickem's. Enhanced offense pick'em contests may be referred to as enhanced O-UP pickem's. Enhanced combined pick'em contests may be referred to as enhanced pickem's.

Pick'em Predictions

Users will predict a combination of the following values for one team in each matchup:

D-UP Stats—Users will make predictions for all D-UP stats according to the D-UP stats list.

O-UP Stats—Users will make predictions for all O-UP stats according to the O-UP stats list.

Enhanced D-UP Stats—Users will make predictions for all enhanced defense stats based on the enhanced pick'em defense stats list.

Enhanced O-UP Stats—Users will make predictions for all enhanced offense stats based on the enhanced pick'em offense stats list.

Final D-UP Score—this score will be calculated based on the base D-UP S stats predicted.

Final O-UP Score—this score will be calculated based on the base O-UP stats predicted.

+1D Score—this field will be calculated based on the sum of the D-UP score and the game score.

Game Winner—user will pick which team will win the game, a user can predict the score for a team that will not necessarily be the game winner. This prediction will be used as a tie breaker in the event that players have the same ranking at the end of a round.

Contest Duration

When creating a contest the user who sets it up will decide on the duration of the contest. Contests may contain several rounds depending on the contest duration. Contest duration options are:

One Day Contest—User will select the date for the contest. User will select the matchups that will be considered for this contest from the matchups that are available on the selected date. All matchups that are included in the contest would be available to choose for this contest.

Weekly Contest—User will select the week for the contest. User will select the matchups that will be considered for this contest from the matchups that are available for this week.

Season Contest—Season pick'em contest creation may be limited to the admin user. Season contests will be organized per game round. Since every team plays the same number of games, each game number will be considered a round of contest play All picks must be made before the first game of the round is played.

Pick'em Contest Results

Each matchup prediction will generate a D-UP and O-UP accuracy score. All match-up predictions for each round of a pick'em contest will result in a final D-UP and O-UP score which would optionally be enhanced by the enhanced stat predictions. Players will be ranked at the end of each round. If there is a tie between two players, the player with the most amount of correct game winner selections will be ranked ahead of the other. At the end of a pick'em Contest, players will be ranked according to the average D-UP and O-UP accuracy of their predictions for each round or contest play. If there is a tie between two players at the end of the contest, the player with the most total correct game winner selections will be ranked ahead of the other.

Contest Setup

There are several options that will be available to both contest types. These options must be selected during the initial contest creation.

Max Entries

When setting up a contest, the user will be able to determine how many entries will be allowed for the contest. There are two special modes for max entries:

Multiplayer—this mode will allow for three or more players to compete in a contest. The possible values for the max entry field will be determined according to a predetermined set of values defined in the max entry schedule. For regular users, possible max entry values will have a direct relationship to the badge level of the user creating the contest.

Head to Head—this mode will allow for only two players to compete in a contest. Max entry field will be preset to two players.

Entry Fees

This is the amount of money that a user will be required to pay in order to participate in a contest. Regular users will be required to pay this entry fee in order to create a contest and will automatically be entered into the contest. This does not apply to admin and celebrity users The possible values for the entry fee will be determined according to a predetermined set of values defined in the entry fee schedule. The range of entry fees will be determined by the number on max entries for the contest. For regular users entry fees will have a direct relationship to the badge level of the user creating the contest.

Prize Structure

When setting up a contest, the user may select what prize structure to implement for contest winners. The possible values for prize structure will be determined according to the prize structure options schedule. Prize structures will be defined in the prize structure definition schedule. The possible values for a specific contest's prize structure options will be determined based on the amount of max entries for the contest.

Minimum Entries

This is the minimum number of contest participants who must enter a contest for it to be able to start. Contests that do not meet the minimum number of entries will be canceled and all entry fees will be refunded to users who did enter the contest. This field will be automatically determined by the platform according to the selected min entry schedule. This field will be predicated by the max entry value selected. This value will not be visible during contest creation to the user setting up the contest.

User Achievements

Throughout the Plus 1D platform users will be able to accumulate various achievements. These achievements will come in the form of various accumulated "IQ" levels as well as badges that will be unlocked based on experience. User IQ levels are based on user performance in contests. User badge levels are based on user experience which is determined according to the number of contests played on the platform.

Cumulative IQ Rankings

D-UP Ranking IQ—This is the accumulated "IQ" level that the user has obtained throughout all defense based contests and pick'em contests. This value will be the average of all base D-UP ranking results for all contests the user has participated in. This value will take into account all enhancements applied to the final D-UP result for determining contest ranking during all participating contests.

O-UP Ranking IQ—This is the accumulated "IQ" level that the user has obtained throughout all offense based contests and pick'em contests. This value will be the average of all base O-UP ranking results for all contests the user has participated in. This value will take into account all enhancements applied to the final O-UP result for determining contest ranking during all participating contests.

Enhanced Ranking IQ—This is the accumulated "IQ" level that the user has obtained throughout all enhanced contests in which the participated. This value will be the average of all enhanced ranking results for all enhanced contests the user has participated in. This value will consist of the average defense enhanced and offense enhanced accuracy rating. Defense only enhanced, offense only enhanced, and complete enhanced results will be averaged together to obtain this value.

Stat Knowledge IQ—This value will be calculated based on the D-UP ranking IQ, O-UP ranking IQ, and enhanced ranking IQ. Both the D-UP and the O-UP rankings considered for this calculation will have already received any enhancement benefits and will be recorded at the end of the contests according to the enhanced score logic schedule. This value could be calculated according to the following formula: (D-UP ranking IQ+0-UP ranking IQ)/2.

User Ranking Level

Users will receive a comparative rank based on the number of contests in which the user has participated. Rank level ranges will be defined in to the user rank schedule. User rank will be determined based on the overall number of contests in which the user has participated. User rank may also depend on the user's stat IQ. A minimum stat IQ will be required to achieve each rank level. A minimum number of played contests will also be required to achieve a level rank. It will be possible for users to move both up and down in ranking. A user who has achieved a specific level may fall to a lower level if his stat IQ were to drop below the level threshold.

Team Rankings

In order to properly asses team performance and provide accurate information to users regarding the team's performance, the teams will be ranked. All teams will be ranked according to each individual stat that is tracked in the platform. All defensive rankings including those produced by both D-Up and enhanced defense stats will be averaged together to determine the team's overall defensive ranking. All offensive rankings including those produced by both O-Up and enhanced offense stats will be averaged together to determine the team's overall offensive ranking. The team's overall+1D ranking will be determined by averaging both the defensive and offensive rankings. Users will be able to review each team's current individual ranking for all Stats as well as the team's overall defensive and offensive rankings when selecting a team for a contest entry.

The following are examples of categories of football defensive stats:

D-UP Stats List:
1. Fumble Recovery
2. Interception
3. 3rd Down non Conversion Punts
4. 4th Down non Conversion Stops
5. 2-point Conversion Stops Enhanced Defense Stats List:
1. Total Points Allowed
2. Special Team Points Allowed
3. Points Allowed Q1
4. Points Allowed Q2
5. Points Allowed Q3
6. Points Allowed Q4
7. Points Allowed First Half
8. Points Allowed Second Half
9. Points Allowed Overtime
10. Defensive Touchdowns
11. Q13 Turnover Sacks
12. Possession Time Allowed
13. Passing Yards Allowed
14. Rushing Yards Allowed
15. Penalty Yards Allowed
16. Opponent Penalty Yards
17. Total Turnover Margin Enhanced Pick'em Defense Stats List:
1. Total Points per Game
2. Possession Time Allowed
3. Passing Yards Allowed
4. Rushing Yards Allowed
5. Special Team Points Allowed
6. Penalty Yards Allowed
7. Q13 Turnover Sacks
8. Defensive Touchdowns The following are examples of categories of football offensive stats:

O-UP Stats List:
1. Touchdowns
2. Field Goals
3. Extra Points
4. 2 Point Conversions Enhanced Offense Stats List:
1. Total Points
2. Special Teams Points
3. Overtime Points
4. Total Possession Time
5. Total Passing Yards
6. Total Rushing Yards
7. Total Yards
8. Yards per Play
9. Passing Attempts
10. Rushing Attempts
11. Total First Downs
12. Penalty Yards
13. QB Turnover Sacks Allowed Enhanced Pick'em Offense Stats List:
1. Total Possession Time
2. Total Passing Yards
3. Total Rushing Yards
4. Special Teams Points
5. Penalty Yards
6. QB Turnover Sacks Allowed
7. Total First Downs
8. Total Points The following are examples of categories of basketball defensive stats:

D-Up Stats List:
1. 24 sec Shot Clock Violation
2. Charges
3. Steals
4. Backcourt Violations
5. 5 Second Inbound Violations
6. Illegal Defense Violation
7. Defensive Rebounds
8. Traveling Violation
9. Missed Free Throw
10. Jump Ball Possession Enhanced Defense Stats:
1. 3-Point Plays
2. Total Points Allowed
3. Total Time of Possession Allowed
4. Total Points Allowed Q1
5. Total Points Allowed Q2
6. Total Points Allowed Q3
7. Total Points Allowed Q4

8. Total Points Allowed First Half
9. Total Points Allowed Second Half
10. Total Missed Free Throws
11. Blocked Shots
12. Missed Final Foul Shot Rebounds Enhanced Pick'em Defense Stats:
1. 3-Point Plays
2. Total Points Allowed
3. Total Time of Possession Allowed
4. Total Missed Free Throws
5. Blocked Shots
6. Missed Final Foul Shot Rebounds The following are examples of categories of basketball offensive stats:

O-UP Stats List:
1. 3-Point Plays
2. 2 point Plays
3. 1-Point Plays
4. Free Throws Enhanced Offense Stats:
1. Total Points
2. Total Points Q1
3. Total Points Q2
4. Total Points Q3
5. Total Points Q4
6. Total Points First Half
7. Total Points Second Half
8. Total Overtime Points
9. 3 Second Lane Violation
10. Free Throw Percentage
11. Assists
12. Offensive Rebounds
13. Flagrant Fouls 1
14. Flagrant Fouls 2
15. Traveling Violations
16. Backcourt Violations
17. Total time of possession Enhanced Pick'em Offense Stats:
1. Total Points
2. Free Throw Percentage
3. Assists
4. Offensive Rebounds
5. Total time of possession The following glossary of terms may aid in a more complete understanding of the present invention:

Stat Knowledge—The knowledge of the game based on Plus 1D unique scoring metric(s).

Overall Stat Knowledge IQ—The overall score/ranking of the stat knowledge which is based on a formula that averages out your D-UP/O-UP point value as is after enhancement participation.

Squad—Squad is defined as the defensive and/or offensive combinations that make a team in fantasy pick'em.

Pick-Em—is defined as the way to play. There are two ways to play.

D-Up—Is a point process based on defensive scoring by design and core ranking value for game play, i.e. non-scoring forced possession changes.

O-Up—Is a point process based on existing offense scoring models, field goals, touchdowns, safeties, etc.

Pick'EM—(specific ways to play):

Straight Pick'em—Player chooses one team and has the option to play enhanced defense or offense. The player can play head to head or multi-player.

Straight League Tournament—Player chooses the league predictions for all sixteen matchups based on one team. The player can play head to head or multi-player.

Fantasy Pick'em—Player chooses team or squad. Players can play head to head or multi-player.

Fantasy League Tournament—Player chooses the league predictions for all sixteen matchups based on any team. User can play head to head or multi-player.

Enhanced Offense—An option to play in D-UP & O-UP that will allow the user an opportunity to increase their stat knowledge IQ. The results may add a weighted value to the D-UP (point) score or O-UP (point) score based on enhanced weighted chart formula.

Enhanced Defense—An option to play in D-UP & O-UP that will allow the user an opportunity to increase their Stat Knowledge IQ, results will add a weighted value to the D-UP (Point) Score or O-UP (Point) Score based on Enhanced Weighted Chart Formula Straight Pick'Em—One Team Where user plays any of the following combinations: D-Up only; D-Up defense enhanced; D-Up defense enhanced with offense enhanced; O-Up only; O-Up offense enhanced; D-Up offense enhanced plus defense enhanced.

Fantasy Pick'Em—Any team (or squad) where user plays any of the following combinations: D-Up only; D-Up defense enhanced; D-Up defense enhanced plus offense enhanced; O-Up only; O-Up offense enhanced; D-Up offense enhanced plus defense enhanced.

In fantasy pick'em users may choose from a defensive squad or offensive squad that are not playing each other. Any future or past game may be selected for gameplay.

D-Up Based

Straight Pick-Em (Team Specific)

Team Specific—The player can pick one team and put in predictions for daily, weekly, season long stats to be ranked and wagered against. Predictions selection tabs include: D-Up with point based/accuracy value (non-scoring forced possession changes).

D-Up Enhanced—Weighted based/accuracy value of stat knowledge (Keeping within the predicted yards).

Offense—Weighted based/accuracy value of stat knowledge (Keeping within the predicted yards) and weighted based/accuracy value of stat knowledge.

Fantasy Pick-Em (Not-Team Specific)

Not Team Specific—User can pick any team offense and any team defense and put in predictions for daily, weekly, season long stats to be ranked and wagered against.

Predictions Tabs Include—D-Up point based/accuracy value (non-scoring forced possession changes).

D-Up Enhanced—Weighted Based/Accuracy Value of stat knowledge. Keeping within the predicted yards.

Offense—Weighted based/accuracy value of stat knowledge. Keeping within the predicted yards. Weighted based/accuracy value of stat knowledge.

O-Up Based

Straight Pick-Em (Team Specific) Team Specific—User can pick one team and put in predictions for daily, weekly, season long stats to be ranked and wagered against.

Predictions Tabs Include:

O-Up—Point based/accuracy value (non-scoring forced possession changes).

O-Up Enhanced—Weighted based/accuracy value of stat knowledge (Keeping within the predicted yards).

Defense—Weighted based/accuracy value of stat knowledge (Keeping within the predicted yards).

Fantasy Pick-Em (Not-Team Specific)

Not Team Specific—User can pick any team offense and any team defense and put in predictions for daily, weekly, season long stats to be ranked and wagered against.

Predictions Tabs Include:

O-Up—Point based/accuracy value (non-scoring forced possession changes).

O-Up Enhanced—Weighted based/accuracy value of stat knowledge. (Keeping within the predicted yards).

Defense—Weighted based/accuracy value of stat knowledge (Keeping within the predicted yards).

Examples of weighting formulations are demonstrated in FIG. 5. This is merely an example and other values could reasonably by substituted within the framework discussed herein.

The present invention is a system and a method that captures sports statistical data through a binary process in real time or with an absolute predetermined number value that is utilized for comparing accuracy of predicting ranking, scoring and wagering against players, squads, teams or individuals. This can be done in fully in real time or retro actively for previously played games versus present, live games.

To better understand the examples in the drawings it should be understood that a 'squad' generally refers to the active players on the field (or other playing surface) for a particular team. A defensive squad or offensive squad is a set of team members that work together as a team. Generally, the adjective 'defensive' denotes that the team is tending to act at that moment to prevent the other team from scoring as contrasted to actively pursuing scoring itself.

For example, in football there are a set of players that are generally referred to as a defensive team and another set referred to as an offensive team. However, the nature of a single play can switch a player or team from being in a defensive posture to an offensive posture very quickly. To illustrate, a quarterback and receiver combination are often thought of be in an offensive role for a given play. But, if in that same play the pass is intercepted then the player who intercepted the ball is now in an offensive role by nature of having possession of the ball with the intent and motivation to attempt to score for his team.

In a similar manner, a hockey player can at one moment be making an offensive drive toward the opposing goal and then be stripped of the puck and is instantly then, with the rest of his team, defending against his opponent and protecting his own team's goal.

Returning to FIG. 1, it can be observed that it basically includes a series of observations of a game of both teams, each having an offensive squad and defensive squad. In FIG. 1 a portion of the game is depicted. In step 12 a first team's offensive squad and an opposing second team's defensive squad compete against each other during a game.

By mere way of illustration a football game is used to flesh out an example. Virtually any sport or other contest could also be fit into this method.

At step 14, throughout the game an observer, such as a scorekeeper or referee, observes the first team's offensive squad for an offensive scoring event. In this football example the offensive scoring event could be a touchdown, field goal, safety, extra point or conversion. In this sense the scoring is similar to a typical and well known football game scoring system.

When an offensive scoring event is detected, meaning observed by the scorekeeper, referee or other game official then a predetermined numerical value associated with that offensive scoring event is awarded. For example six points to the team whose offensive squad scored the touchdown.

This score is then recorded in a computer readable medium. This could be a score keeping computer. With similar effect the score could be recorded on paper with pencil or other available means to record the fact that points were awarded to a team. Then, that predetermined numerical value, the points awarded, is added to a first sum which is the overall score for that team. The score is then recorded in a computer readable medium where it can be saved, recalled and have additions made for future scoring events for that team.

During the same course of play as described immediately above in step 14, the present method materially departs from all known processes and methods to evaluate a team in step 16.

In step 16, throughout the game an observer, possibly the same or similar official or referee as observing the other team's offense, observes the second team's defensive squad for a defensive scoring event. For example a touchdown, a two point non-conversion, non-converting on special team points, blocking an extra point, other turnover, fumble recovery, interception, a forced quarterback turnover sack, forcing a punt, a safety, a touchback, a fourth down non-conversion or any time an opposing team, squad or player in an offensive role fails to produce points from a possession change.

To elaborate for clarity of one scoring event, forcing a punt is important in a football example. Under the traditional rules, when a team in possession of the ball is considering their options on a fourth down, they can attempt an advancing play for a new down or can punt the ball downfield. The punt downfield will normally result in turning possession to the receiving team and put that receiving team far from the opposing goal. Obviously, this makes a long run for their offensive chances during their possession.

Continuing this example, in the present system, the offensive team situated with a fourth down is now faced with the reality that a punt will give a point (or two) to the receiving team for having forced a turnover of possession. Now, there may be pressure for the offensive team on a fourth down to attempt to advance the ball and retain possession rather that punt downfield a relinquishing possession.

Further in this example, with an offensive team on a fourth down it may be possible to attempt a field goal. The probability of a successful field goal decreases with the distance from the goal posts. An unsuccessful field goal attempt may be a defensive scoring event for forcing the other team into that precarious position. On the other hand, a successful field goal should not reward the defense.

As can now be seen, the pressures and strategic thought process may be different than under traditional rules. The action of the game will be increased. The likelihood of a tie and subsequent overtime will be similarly reduced.

It should be noted that in the traditional football scoring rubric defensive successes are typically not awarded points to the defending team. In this presently described arrangement the fruitful behavior and achievements of the defense contributes to the overall score of the whole team.

It should now be appreciated that an offensive squad may now have pressure to behave differently. Instead of having relatively low point risk for play that might expose the quarterback to a turnover sack, now the offense could be exposed to consider their respective defense to protect the integrity of the quarterback.

In another one of many possible repercussions of this new scoring method, a team may have different considerations when deciding whether to punt or make a play to advance the ball on their own terms when faced with a fourth down situation.

In a sense, the lines of distinction between which is the offensive squad and which is the defensive squad are blurred. Both offense and defense can now score and both offense and defense can risk giving away points by certain actions.

Returning to the example, when a defensive scoring event is detected, again by the scoring official, then a predetermined numerical value associated with that defensive scoring event is recorded in a computer readable medium. Similar to offensive scoring that recording is commonly done with a computer and appropriate software or by other available recording means. That predetermined numerical value is added to a second sum, the score of the team now characterized as defensive, and recorded in a computer readable medium.

Continuing this example in step 18, a swap of each teams' defensive squad for offensive squad and offensive squad for defensive squad is shown. This is a familiar event in football as the team with possession of the ball shifts from one team to the other as squads are exchanges on the field. As noted above, this characteristic role of being offense or defense does not necessarily mean a change of the players on the field. This is because a single player at one moment can be either defensive or offensive and then, due to the course of events of a play, can change to the converse role.

In similar fashion to steps 14 and 16, above, steps 20 and 22 show that both the offensive squad of the second team as well as the defensive squad of the first team each now have an opportunity to score points for their respective teams.

When a predetermined action, such as a touchdown, a two point non-conversion, non-converting on special team points, blocking an extra point, other turnover, fumble recovery, interception, a forced quarterback turnover sack, forcing a punt, a safety, a touchback, a fourth down non-conversion or any time an opposing team, squad or player in an offensive role fails to produce points from a possession change. Likewise, when a fumble recovery, interception or other turnover, a quarterback turner sack or stripping the ball occurs then the defensive squad responsible for that action is credited with achieving points for the team overall and that teams score is appropriately increased with that predetermined numerical value (points).

Figure 2:
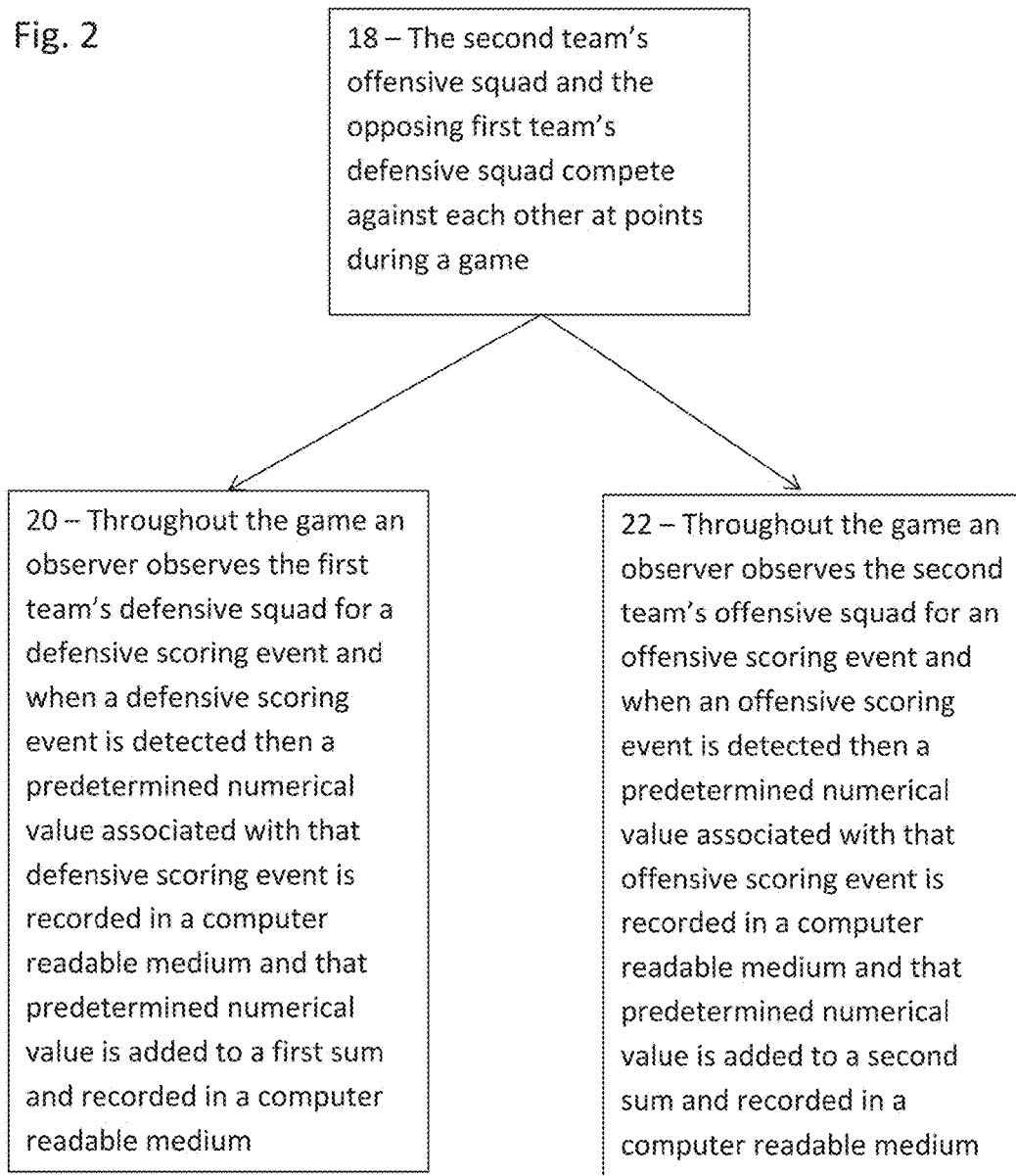
FIG. 2 shows a flow chart of a part of a process.

As with the scenario in FIG. 1, the converse field in FIG. 2 also has the points recorded in a computer readable or human readable medium and that teams score is summed to reflect the total points earned by both the defense and offense of that team.

Figure 3:
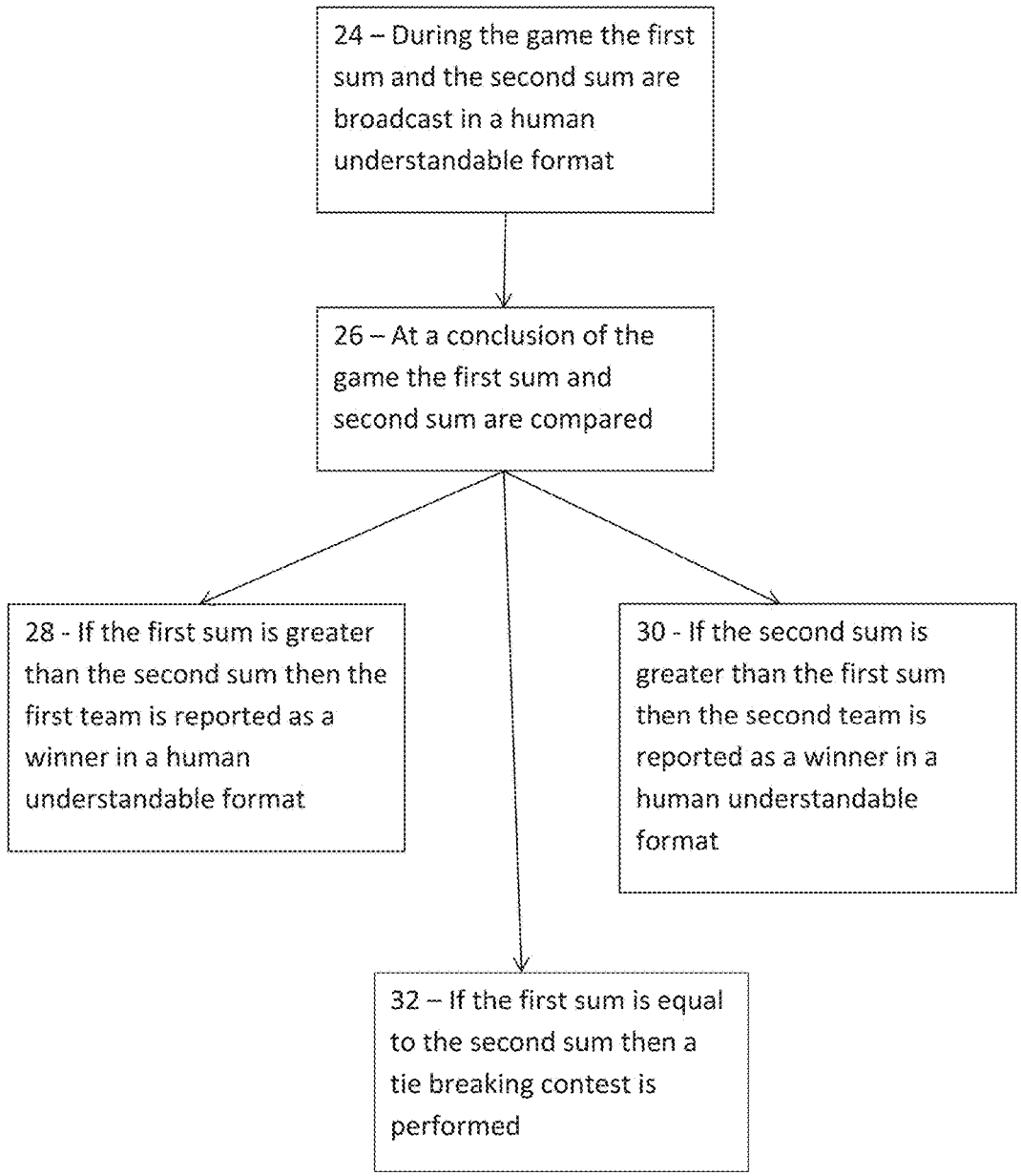
FIG. 3 illustrates a flow chart of part of a process.

FIG. 3 continues with this football example, in step 24 at least at some point during the game the sums or scores for the first and second teams are displayed in a human readable format. This could be done by means of a visual display, such as score board. An alternate format that could be understood by a person could be an audible broadcast of the then current scores.

Step 26 is contemplated at the end of the regularly timed play. For example, the clock on the fourth quarter has finally run out, typically the end of regulation play. It is at this point that the winner and loser of the game are determined, recorded and announced.

Steps 28, 30 and 32 show the three possible outcomes at the end of the regulation clock. In step 28 the first team prevails and this is reported on the score board or other humanly understandable announcement. In step 30 the second team has a greater score and prevails and this outcome is similarly proclaimed. Or, in step 32 the first team and second team have the same score.

It should be noted that with both defensive and offensive teams theoretically scoring points throughout the game that a 'tie', as in step 32, is a relatively unlikely outcome. However, in the event of equal scores then a special contest can be determinative of the final result. For example, a sudden death situation where the next team to score any point could be the prevailing team. Other tie breaking events could also be employed and remain within the scope of this invention.

It should be understood that this method and system of comparing teams can be applied to other sports. For example, in baseball the defensive team is on the field while the offensive team is at bat. Under the historical rules, only the batting team can score by earning run. The excellence of the defense cannot directly score, although they can benefit their team by limiting the opposing team's scoring opportunities.

Continuing this baseball example, by using the presently described approach, a defensive scoring event could be, for example, when a pitcher pitches a no hit inning, thus awarding that pitcher's team a point (run) or two. Another defensive scoring event might be a double or a triple play by the fielders. Again this could be worth a preset value. Other defensive plays that show the excellence of a defensive play could equally be characterized as a defensive scoring event.

A version of the present invention can be fairly described as a method for ranking performance of a sports team during the course of a single game comprised of the steps of observing a first team in an offensive role for a first scoring event and then assigning that first scoring event a predetermined first numerical value. This first numerical value is recorded in a computer readable medium, such as a computer and adding it to a first sum. The first sum is essentially a running tally of the total points achieved by the first team. Simultaneously, an observer observes a first team in a defensive role for a second scoring event. The defensive role is generally defined by the team at the moment with the traditional role of preventing the opposing team from scoring or gaining an advantage. The second scoring event is assigned a predetermined second numerical value. That value, and all the scoring event values are decided before play begins. The second numerical value is recorded in a computer readable medium and adding it to a first sum. Likewise and at the same time a second team is observed in an offensive role for a third scoring event and then the third scoring event is assigned a predetermined third numerical value. The third numerical value is recorded in a computer readable medium and adding it to a second sum. The second sum is essentially a score of the second team. Simultaneously, a second team is observed in a defensive role for a fourth scoring event and once detected then the fourth scoring event is assigned a predetermined fourth numerical value. The fourth numerical value is recorded in a computer readable medium, such as memory in a computer, and is then added to a second sum. Also simultaneously during the game broadcasting the first sum and the second sum are broadcast in a human understandable format such as audibly or visually. At the end of the game the first sum and second sum are compared and broadcast in a report with the team with a greater score identified as a prevailing team.

In a version of this method the defensive scoring event is any of a a touchdown, a two point non-conversion, non-converting on special team points, blocking an extra point, other turnover, fumble recovery, interception, a forced quarterback turnover sack, forcing a punt, a safety, a touchback, a fourth down non-conversion or any time an opposing team, squad or player in an offensive role fails to produce points from a possession change.

As is now apparent, a team or individual athlete in a defensive role may be awarded a predetermined point value score for forcing a non-scoring possession change of the game ball (or puck or other game object). The fantasy sports player or bettor then makes a prediction of the amount or value of the defense's role in forcing a non-scoring forced possession change. At the conclusion of the game the actual value of non-scoring possession changes is compared to the predicted non-scoring possession change values and an intelligence quotient (IQ) is derived. The game-player may then be compared to her other predictions or may also be compared to other game-players. The closer the game-player's predictions are to the actual result the more stat knowledge that game-player is determined to possess.

Essentially, players, squads or teams that are in a defensive role are assigned value of the defense performance. A fantasy game-player can predict the outcome. The more accurate the game-player's prediction the more intelligent that game-player is and accordingly prevails over lesser accurate predictions from other players. The traditional points scored by the offensive squads a not factored into the stat IQ. Similarly, the actual outcome of the games using traditional scoring means is not relevant as only the game-players predictions are valued as compared to the actual non-scoring possession changes point values.

Notice that one of the athletes (or teams) will score on any possession change. Often this is the normal game play where when a team scores then possession passes to the other team. However, in the present method, only non-scoring possession changes are valued. Non-scoring possession changes by nature are done by excellence of the defensive role.

The present invention is generally internet driven in that managed server computers that connect to individual game players' devices. The game players can use personal computers, handheld devices, phones or any other means to navigate and interact electronically with the server computers. Parts or all of the software components may be hosted on the server computer. Some parts of the software package may also be installed onto the player's device that can facilitate the interaction communicating with the server.

Although internet network communication is preferred for wide scale deployment of the system, the software can be run on a single device, on a local network or other communication protocol if multiple players engage the system simultaneously.

In an important version of the system the primary computing power and proprietary software is housed on an internet connected server. A client application software is installed on a game player's personal computing device. The client application software interacts over the internet with the server. This improves security of the system, allows for updates to be immediately deployed system-wide without further interaction by the end user game player.

The system can be described computer based method for single squad team fantasy matchup pools quantifying a game-player's prediction skills and statistical knowledge of defensive athletic performance comprised generally of the steps of the player affirmatively accessing the system with a uniquely identified account then selecting a single team or multiple teams that the user wishes to include in a new contest then the user enters in predictions of various quantifiable aspects of game play (for example, defensive scores, ranking, times, offensive scores, overall scores). After the actual athletic plays are complete or in real time as the physical games are played the actual aspects are compared on the server to the predicted results. A final value is tabulated and presented to the gameplayer and may also be compared to other competing players or the same game-players prior results.

Non-scoring force possession changes (NSFPC) are performed by a squad, team or player in a defense defensive role that prevents an offense from scoring, for example, a touchdown, a two point non-conversion, non-converting on special team points, blocking an extra point, other turnover, fumble recovery, interception, a forced quarterback turnover sack, forcing a punt, a safety, a touchback, a fourth down non-conversion or any time an opposing team, squad or player in an offensive role fails to produce points from a possession change. These are examples derived from football and other events may be used for football or as appropriate for other types of sporting events. Generally, these events are reflective of superior performance of a team, squad or individual in a defensive role during game play.

The NSFPC score is tabulated by the server computer live during the subject athletic event or after its conclusion. The NSFPC score is calculated against the gameplayer's predictions to determine degree of accuracy for an ultimate result.

There are multiple types of fantasy games to which process may successfully applied. One example is pick'em single squad matchup pools. The game player selects her team, squad or players anticipated ranking among other corresponding teams, squads or players. Looking at the table shown in FIG. 6, a percent factor is assigned for the difference in actual defense up (DUP) and/or offense up (OUP) ranking and the prediction made by the game player.

Defense base stat contests will be referred to as D-UP (or DUP) Contests. Offense base stat contests will be referred to as O-UP (or OUP) contests. Combined base stat contests will be referred to as combined stat contests. Users (also referred to as game players) will predict the number of these events that may occur throughout a game and will be ranked on how accurately they predict the number of these events.

D-UP (defense up) score—this is the score obtained from the base stat predictions in a defense based contest. This will be the final score for a D-UP Contest. This score will be added to the user's average D-UP score. This score will determine the winner for the D-UP contest.

Enhanced Score—this is the score obtained from the enhanced stat predictions in a contest.

Enhanced D-UP Score—this is the score obtained when taking the base D-UP score and applying any modifications offered by the enhanced score results. This will be the final score for a D-UP enhanced contest. This score will be added to the user's average D-UP score. This score will determine the winner for the D-UP Enhanced contest.

O-UP (offense up) score is the score obtained from the base stat predictions in an offense based contest. This will be the final score for an O-UP contest. This score will be added to the user's average O-UP score. This score will determine the winner for the O-UP contest. Enhanced scores ares the scores obtained from the enhanced stat predictions in a contest. An enhanced O-UP score is the score obtained when taking the base O-UP score and applying any modifications offered by the enhanced score results. This will be the final score for an O-UP enhanced contest. This score will be added to the user's average O-UP score. This score will determine the winner for the O-UP enhanced contest.

For example, if the gameplayer predicted that a team would end the week ranked as the fourth best in the league but that team ended up at either the third or the fifth ranked in the league then, as referenced in the FIG. 1 table, the percent factor is ninety percent. This is determined because the game players prediction was one off from the actual team ranking.

Similarly, if the game player's prediction turned out, at the end of the week or other predefined period, to be three spots away from the actual rank result then the percent factor is seventy percent. Note that for any prediction that is ten or more positions away from the actual ranking then the percent factor would be zero.

For any pick'em contest the nature of the contest can be DUP, OUP, or DUP/OUP. The user or game player selects matchup to predict any of the following:
DUP
OUP
Win/Loss/OT (overtime) Win/OT Loss/OT Draw This can also be done for professional football or basketball for each squad, team or individual player as the game player selects. Ranking for each squad, team or player may similarly be the basis for the performance prediction.

For each matchup the score is calculated by averaging the prediction accuracies of DUP or OUP, DUP/OUP combined and includes the weekly ranking percentages. The points from WIN/LOSS/OT Win/OT Loss/OT Draw are added to the matchup average percentage. Based on the total number of squads in the pool some of the wagering options may or may not be available for predictions.

Correctly predicting any of WIN/LOSS/OT Win/OT Loss/OT Draw awards the game player a one hundred percent factor for this aspect of the wager. Incorrectly predicting any of these results in a zero percent factor. Predicting the correct result of a win or a loss but being incorrect on whether that results happens in regular play or during overtime gives the game player a fifty percent factor.

For predicting the points awarded to a team, squad or player the percent factor is determined by the ration of the predicted compared to the actual value. For example, if the game player predicted a twenty point score and the actual score was ten points then the resulting percent factor would be fifty percent. Similarly if twenty was predicted and the actual score was fifteen then the percent factor would be seventy five percent, reflecting a closer prediction to the actual score.

For example, a DUP contest matchup the user scores 80% DUP, 90% ranking, and correctly predicts a win. The matchup score would be 86%.

Another example, a DUP/OUP contest matchup the user scores 70% DUP, 80% ranking, correctly picks that squad to win, then a 80% OUP, 70% ranking, and correctly picks that squad to lose. The matchup score would be 77%.

For the total contest score, all the matchup percentages are averaged. Thus, if a game player achieves matchup scores of 40%, 50%, 70% and 80% then the average would be 60%. Similarly if the matchup scores were 80% and 90% then the total contest score would be 85%.

Team Fantasy Single squad matchup prediction pools may be characterized in the following categories:
Defense only/squad ranking
Offense only/squad ranking
Combine straight/overall ranking
Combine fantasy/overall ranking
Squad prediction outcome
Points allowed
Points scored
Squad ranking (post games)

Team fantasy single squad matchup predictions pools compare offense only, defense only or combine straight or fantasy offense and defense. Real time or existing known outcomes may be the basis for tabulating the squad's score. Alternative ways to play both real time and fantasy are included.

Any single defensive squad real time actual statistical results vs any single offensive single squad actual statistical results compared to individuals/players predictions of that single squad same or different fantasy real time statistical outcome/results that's based on your predictions accuracy which are captured and recorded as stat knowledge IQ. That's result can be wagered against other individuals/players stat knowledge IQ.

Any single squad or combined existing known statistical outcome may be compared to any single or combined real time statistical outcome. The difference between existing and real time outcomes is an important feature of the system. A game player may create an actual difference in the statistical outcome in which individuals or players make predictions against them.

Retro version allows any past known single squad (or game or player) statistical outcome to be compared to any real time single squad statistical outcome. The difference between the existing known statistical outcome and real time statistical outcome results that individuals/players make predictions on that statistical difference based on a real time single squad statistical game play. Participant individuals/players make a prediction on the actual results. That result can be wagered against other individuals/players stat knowledge IQ (intelligence quotient).

A single squad may include all component individual athletes, positions only or combined with or without special teams. An alternative way of playing rank'em is found where the enhanced feature allows players to increase their score by ten percent optionally if the player is one hundred percent accurate their over all score is increased by ten percent. If they are over or under by ten places the score equals zero.

The cumulative score is applied to the enhanced weighted system. The system is predicated on the number of contests. Enter the cumulative score is between fifty five and forty five percent and remains the same. This is related to the enhanced weighted system described herein.

The enhanced button is preferably on the predictions page so that plays are optionally base or enhanced. Each contest is individually weighted within a pool. A player should have the option up to, for example, one hour before a selected contest O-up or D-up to enhanced or base stats.

There may also be included an only button. The number of possession D-up or O-up is preferably be part of stats overall or individually.

A version of the invention can be fairly described as any single squad including all components, athlete, positions only or combined with or without special teams or with or without players participation that can be utilized for wagering, scoring, ranking that can be compared with or against any single squad athlete, positions only or combined with or without special teams that can be ultimately captured through predictions and displayed as stat IQ pools or individual contest for comparing and contrast for individuals stat knowledge IQ. This can be done in real-time or in retro mode for previously played contests.

A method of comparing game-players of competitive sports statistics wagering. The game-players apply skill and their knowledge of sports statistics to predict an outcome of value provided to a team or individual while in a defensive role. Generally, football players in a defensive role are attributed a value based on forcing a non-scoring possession change. That actual value is compared to the game-players' predicted value. The game-players may be ranked on the accuracy of their predictions. The statistics may be provided for teams, squads or individuals playing against each other or in different games.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A computer based method for quantifying a game-player's prediction skills and statistical knowledge of defensive athletic performance, the method comprising the steps of:
   during a first game observing a first team in a defensive role for a first scoring event during a first play against a second team in an offensive role;
   the first scoring event is only a formerly non-scoring forced possession change from the second team to the first team;
   the possession change is determined only at a conclusion of the first play;
   assigning to the first scoring event a predetermined first numerical value;
   recording on the computer the first numerical value in a computer readable medium and adding it to a first sum;
   prior to the first game the first sum is zero and at a conclusion of the first game the first sum is a first total;
   during a second game observing a third team in a defensive role for a second scoring event during a second play against a fourth team in an offensive role;
   the second scoring event is only a formerly non-scoring forced possession change from the fourth team to the third team;
   the possession change is determined only at the conclusion of the second play;
   assigning to the second scoring event a predetermined second numerical value;
   recording on the computer the second numerical value in a computer readable medium and adding it to a second sum;
   prior to the second game the second sum is zero and at a conclusion of the second game the second sum is a second total;
   before the first game is commenced a first game-player enters a numerical prediction of the first total that is recorded on the computer;
   before the second game is commenced a second game-player enters a numerical prediction of the second total that is recorded on the computer; and
   at the conclusion of the first game and second game a first IQ is recorded in the computer as the difference between the numerical prediction of the first game-player and the first total and a second IQ is recorded in the computer as the difference between the numerical prediction of the second game-player and the second total; in response to the first IQ being lesser than the second IQ then the first game-player is identified as prevailing over the second game-player or in response to the second IQ being lesser than the first IQ then the second game-player is identified as prevailing over the first game-player; the computer presents the first IQ, second IQ and identifies the prevailing game-player in a human readable format.

2. The computer based method for quantifying a game-player's prediction skills and statistical knowledge of athletic performance as in claim 1, further characterized in that the defensive scoring event is any of a fumble recovery, interception or other turnover, a quarterback forced turnover sack, forcing a punt, stripping the ball from an offensive player with defense recovery, a safety, a touchback, a fourth down non-conversion, a two point non-conversion, blocking an extra point, blocking a punt or any time a defense prevents an offense from scoring a touchdown or converting a special points team.

3. The computer based method for quantifying a game-player's prediction skills and statistical knowledge of athletic performance as in claim 1, further characterized in that the first game is the same as the second game and the first team is the same as the fourth team and the second team is the same as the third team.

4. A computer based method for single squad team fantasy matchup pools for quantifying a game-player's prediction skills and statistical knowledge of a defensive athletic performance, the method comprising the steps of:
   the game-player makes a prediction of formerly non-scoring forced possession changes where a defense prevents an offense from scoring a touchdown or a two point non-conversion, converting on special team points, blocking an extra point, a turnover, a fumble recovery, an interception, a forced quarterback turnover sack, forcing a punt, a safety, a touchback, a fourth down non-conversion, where a formerly non-scoring forced possession change is a scoring event or the game-player making a prediction of an offense failing to produce traditional points from a possession change is a scoring event;
   the prediction is adjusted by one hundred percent in response to the game-player accurately predicting a win, an overtime win, a loss or an overtime loss or the prediction is adjusted by fifty percent in response to the game-player predicting a win or a loss but incorrectly predicting whether that win or loss was in normal game play or in overtime;
   the prediction is adjusted by multiplying the prediction by quotient of the predicted score divided by the actual score determined after the game is completed;
   the prediction is adjusted by a graduated factor for how closely the game-player predicted the league ranking after a game;
   an adjusted score is tabulated and recorded on the computer;
   the adjusted score from the game-player is compared to an adjusted from another game-player;
   the game-player with the greater adjusted score is determined to be a prevailing game-player;
   the prevailing game-player is identified in a human readable format as a winner;
   any single squad including all components, athletes, positions only or combined with or without special teams or with or without players participation are utilized for wagering, scoring, ranking that is compared with or against any single squad, athlete, positions only or combined with or without special teams that is ultimately captured through predictions and displayed as stat IQ pools or individual contest for comparing and contrast for individuals stat knowledge IQ in real-time or in retro mode for previously played contests;
   team fantasy single squad matchup predictions pools compare offense only, defense only or combine straight or fantasy offense and defense; real time or existing known outcomes are the basis for tabulating the squad's score;
   play modes in both real time and fantasy are provided;
   any single defensive squad real time actual statistical results versus any single offensive single squad actual statistical results is compared to individuals or player's predictions of that single squad same or different fantasy real time statistical outcome or results that are based on the player's prediction accuracy which are captured and recorded as stat knowledge IQ;

the result is wagered against other individuals or players stat knowledge IQ;

any single squad or combined existing known statistical outcome is compared to any single or combined real time statistical outcome;

the difference between existing and real time outcomes is available for game player selection;

a game player creates an actual difference in the statistical outcome in which individuals or players make predictions against those predictions;

a retro version allows any past known single squad or game or player's statistical outcome to be compared to any real time single squad statistical outcome; and the difference between the existing known statistical outcome and real time statistical outcome results in individuals or players making predictions on that statistical difference based on a real time single squad statistical game play;

participant individuals or players make a prediction on the actual results and that result is wagered against other individuals or player's stat knowledge IQ.

5. A process which utilizes single squad matchup predictions pools, formerly non-scoring forced possession changes, binary stats, players participants predictions, real-time or known statistical outcomes that are compared to other squads, teams, individuals, positions, athletes, ranking and wagering based on a single contest or pool cumulative averages the process comprising:

a stat knowledge IQ difference allows players to control the outcome of their participation;

a plus 1D captures both offensive and defensive scores based on a fan's anticipated prediction IQ and not the actual game results, real-time, retro or fantasy;

a self-sustaining validation process;

regardless of whether a selected squad/team is competing, it is a player's stat knowledge IQ that represents the player's team predicted outcome that is compared to other fans prediction IQ's which is recorded; wherein a formerly non-scoring forced possession change is a scoring event;

players are permitted to participate from a pre-season to a playoff including a final game for team sports;

the process is integrated seamlessly into the traditional team sports leagues without any additional revenue cost with a simple rule change by a competition committee;

the process applies to sports wagering in collegiate, professional, live or fantasy;

the process strengthens a league integrity based on increased accountability for an offensive and a defensive squad scoring capability;

players validate their in-game social media sports experiences through stat knowledge IQ in a competitive process to prove or wager.

* * * * *